US012256950B2

(12) United States Patent
Siccardi et al.

(10) Patent No.: US 12,256,950 B2
(45) Date of Patent: Mar. 25, 2025

(54) PATIENT-SPECIFIC GUIDE FOR TOTAL PROSTHETIC KNEE REVISION

(71) Applicant: MEDACTA INTERNATIONAL SA, Castel San Pietro (CH)

(72) Inventors: Francesco Siccardi, Castel San Pietro (CH); Massimiliano Bernardoni, Castel San Pietro (CH); Andrea Parrinello, Castel San Pietro (CH); Gianluca Gargantini, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 500 days.

(21) Appl. No.: 17/602,436

(22) PCT Filed: Mar. 16, 2020

(86) PCT No.: PCT/IB2020/052371
§ 371 (c)(1),
(2) Date: Oct. 8, 2021

(87) PCT Pub. No.: WO2020/208441
PCT Pub. Date: Oct. 15, 2020

(65) Prior Publication Data
US 2022/0167998 A1   Jun. 2, 2022

(30) Foreign Application Priority Data
Apr. 9, 2019   (IT) .................. 102019000005430

(51) Int. Cl.
*A61B 17/17*   (2006.01)
*A61B 17/16*   (2006.01)
(52) U.S. Cl.
CPC ...... *A61B 17/1764* (2013.01); *A61B 17/1615* (2013.01)

(58) Field of Classification Search
CPC .................. A61B 17/155; A61B 17/1764
See application file for complete search history.

(56) References Cited

U.S. PATENT DOCUMENTS

| 10,213,320 B2 | 2/2019 | Olgiati et al. | |
| 2009/0088763 A1* | 4/2009 | Aram | A61B 17/157 606/88 |

(Continued)

FOREIGN PATENT DOCUMENTS

| EP | 2739216 A1 | 6/2014 |
| WO | 2018202271 A1 | 11/2018 |

OTHER PUBLICATIONS

International Search Report and Written Opinion issued in PCT/IB2020/052371, Mailed May 12, 2020, 12 Pages.

*Primary Examiner* — Samuel S Hanna
(74) *Attorney, Agent, or Firm* — Meunier Carlin & Curfman LLC

(57) ABSTRACT

A femoral component and a tibial component are respectively configured to exclusively couple with the distal end of a femur bearing a femoral prosthesis and with the proximal end of a tibia bearing a tibial prosthesis. The femoral component has a distal portion configured to face the distal end of the femur, bearing distal positioning holes facing a distal region of the femoral prosthesis. A frontal portion extends on the continuation of the distal portion and has a first abutment area operating against the femur bone part and a second area facing a frontal region of the femoral prosthesis. The frontal portion has at least two guide holes at the first abutment area, and at least two frontal positioning holes at the second area.

31 Claims, 16 Drawing Sheets

(56) References Cited

U.S. PATENT DOCUMENTS

| | | | |
|---|---|---|---|
| 2014/0257309 A1* | 9/2014 | Aram | A61F 2/3859 |
| | | | 606/88 |
| 2015/0190143 A1 | 7/2015 | Tarabichi et al. | |
| 2017/0007331 A1 | 1/2017 | Couture et al. | |
| 2017/0273718 A1* | 9/2017 | Metzger | A61B 17/58 |
| 2017/0333209 A1* | 11/2017 | Tsukayama | A61F 2/4684 |

* cited by examiner

PATIENT-SPECIFIC GUIDE FOR TOTAL PROSTHETIC KNEE REVISION

This invention concerns a procedure for producing a patient-specific surgical guide to apply a total prosthetic knee revision. The invention also concerns the surgical guide that can be obtained via the above-mentioned procedure, which can be conveniently used in a method for performing a total prosthetic knee revision.

EP 2739216 B1 describes a surgical guide for implanting a knee prosthesis comprising a first component that is exclusively coupled to the distal end of the femoral epiphysis and a second component that is coupled to the proximal end of the tibial epiphysis. The installation of the prosthesis involves pre-operative planning during which the anatomical conformation of the distal end of the femur and the proximal end of the tibia of the patient is detected, typically by means of computed tomography (CT) or magnetic resonance imaging (MRI). The prostheses to be implanted are produced, as well as surgical guides and/or other instruments specifically used for their installation in the patient, are produced based on the anatomical conformations detected.

The surgical guide is produced according to an internal conformation that adapts to that of the distal end of the knee, so that it is suitable for being coupled, according to a unique and predetermined position, to the bone epiphysis. Following the positioning of the surgical guide on the bone epiphysis, a series of pins that can be inserted through the corresponding guide holes arranged in the surgical guide enables the guide to be fixed to the epiphysis. Thus, the required resections can be correctly carried out in order to adapt the conformation of the femoral epiphysis to that of the prosthesis to be installed.

In the prior art, when replacing a prosthesis for a total knee arthroplasty, using conventional metal instruments, the prosthesis already in situ is removed and the femoral and tibial canals are opened using a special drill bit. The finishing of the intramedullary canals of the femur and tibia is then performed using cutters of lengths and diameters chosen specifically according to the size of the femoral/tibial stem to be joined to the new prosthesis, which must be implanted to replace the previous one. Additional work is performed on the distal end of the femur and/or the proximal end of the tibia to reshape the bone portions intended to accommodate the new femoral and/or tibial prostheses.

The presence of the patient's prostheses in the pre-operative planning phases precludes the possibility of adopting the same operating procedures, used in performing the first implant, for the processing of bone portions in order to prepare them to host the new replacement prostheses. In fact, the need to remove the prostheses to process the bone portions results in the loss of geometric references that can be detected via computed tomography or magnetic resonance imaging techniques.

Consequently, the coronal and sagittal plane tilt of the distal femoral cut and proximal tibial cut, which guide the final positioning of the implant and the finishing direction of the intramedullary canals for the extension stems, cannot be planned. The tilt of the bone resections and the direction of the canal finishing need to be manually defined by the surgeon during the operation, based on her/his experience and skills.

If the correct direction for finishing the intramedullary canal is not identified immediately, there is a risk of incorrectly positioning the stem inside the intramedullary canal. This may cause interference between the stem and the cortical bone, resulting in pain for the patient, risk to femoral bone cohesion, and/or difficulty in positioning the femoral and/or tibial component.

WO 2018/202271 and US 2017/0007331 A1 propose patient-specific methods and related tools for applying a revision total knee arthroplasty. The purpose of this invention is to overcome the limits of the prior art, by means of a tool that enables the bone portions intended to accommodate the new prostheses, replacing those previously installed, to be remodeled in a more precise and reliable way.

In particular, we want to offer a tool that enables the cutting guides to be uniquely and correctly repositioned, to recalibrate the resections of the bone ends, despite the presence of the primary prosthesis previously implanted.

In a first aspect, this invention concerns a patient-specific surgical guide to apply a total prosthetic knee revision, according to claim 1 and/or one or more subsequent claims.

In an additional inventive aspect, a preferential process for the production of the surgical guide comprising: detecting the anatomical conformation of the distal end of a patient's femur, wherein said distal end bears a femoral prosthesis; producing a surgical guide according to claim 1, and/or one or more subsequent claims, on the basis of the detected anatomical conformation.

According to an additional aspect of the invention, the surgical guide according to the invention can conveniently be used in a method to apply a total prosthetic knee revision, comprising:

exclusively coupling the femoral component of a surgical guide according to claim 1, and/or one or more subsequent claims, against the distal end of the patient's femur;
  inserting at least two alignment pins into the guide holes of the femoral component and through the front cortical region of the femur;
  removing the femoral component from the distal end of the femur;
  removing the femoral prosthesis from the distal end of the femur;
  engaging said guide holes along the alignment pins to exclusively re-couple the femoral component to the distal end of the femur;
  preparing attachment holes through the femoral bone part, using a drilling tool guided through the frontal positioning holes and the distal positioning holes of the femoral component;
  removing the femoral component from the distal end of the femur;
  engaging frontal and distal positioning pins in the frontal and distal positioning holes, respectively;
  engaging a distal cutting block on the frontal positioning pins;
  performing a distal femoral bone resection while the distal cutting block is engaged on the frontal positioning pins;
  engaging a frontal cutting block on the distal positioning pins;
  performing a frontal resection of the femoral bone part while the frontal cutting block is engaged on the distal positioning pins;
  removing the frontal and distal positioning pins;
  positioning a revision femoral prosthesis on the distal end of the femur.

Before or after implantation of the revision femoral prosthesis the follow actions can, conveniently, be completed by means of the femoral component:

exclusively coupling the tibial component of a surgical guide according to claim 14 and/or one or more of the subsequent claims, against the proximal end of the patient's tibia;

inserting at least two tibial alignment pins into the tibial positioning holes of the tibial component and through the tibia's front cortical region;

removing the tibial component from the proximal end of the tibia;

removing the tibial prosthesis from the proximal end of the tibia;

engaging a tibial resection block on the tibial positioning pins;

performing a proximal resection of the tibial bone part while the tibial component is engaged on the tibial positioning pins;

removing the tibial alignment pins;

positioning a revision tibial prosthesis on the proximal end of the tibia.

In at least one of the above-mentioned inventive steps, one preferred embodiment of the invention may also comprise one or more of the following features.

Preferably, the femoral component also has two lateral abutments bearing third abutment areas configured to act in abutment against the femoral bone part in, respectively, the medial and lateral epicondylar regions of the femur.

Preferably, the lateral abutments have corresponding auxiliary positioning holes extending through the third abutment areas.

Preferably, the lateral abutments are borne at the end by the corresponding brackets protruding from the distal portion.

Preferably, the second area, which can also be identified as the second abutment area, is configured to act in abutment against the frontal region of the femoral prosthesis.

Preferably, the distal portion has at least a fourth abutment area configured to act in abutment against the distal region of the femoral prosthesis.

Preferably, the fourth abutment area is substantially orthogonal in relation to the first abutment area.

Preferably, the first abutment area and the second area respectively extend continuously.

Preferably, the proximal portion has a transverse orientation in relation to the distal portion.

Preferably, the guide holes are configured to smoothly engage corresponding alignment pins that can be inserted through the front cortical region of the femur.

Preferably, the guide holes are each configured to guide the respective alignment pin through the femoral bone part in a position spaced apart from a peripheral edge of the femoral prosthesis.

Preferably, the guide holes are parallel to each other.

Preferably, the frontal positioning holes are each positioned between at least one of either the guide holes or the distal portion.

Preferably, the frontal positioning holes are oriented in their respective axes substantially parallel to the guide holes.

Preferably, the frontal positioning holes are oriented according to respective axes substantially perpendicular to a longitudinal extension direction of the femur, when the femoral component is coupled to the distal end of the femur.

Preferably, the frontal positioning holes are configured to smoothly engage a drilling tool that can be inserted through the femoral bone part when the femoral component is coupled to the distal end of the femur, after removal of the femoral prosthesis, to make holes in the femur that are arranged to accommodate the corresponding frontal positioning pins.

Preferably, the frontal positioning pins are configured to smoothly engage two first centring holes arranged on a removable distal cutting block engaged on the frontal positioning pins after removal of the femoral component.

Preferably, the distal positioning holes are oriented according to respective axes substantially parallel to a longitudinal extension direction of the femur, when the femoral component is coupled to the distal end of the femur.

Preferably, the distal positioning holes are configured to smoothly engage a drilling tool that can be inserted through the femoral bone part when the femoral component is coupled to the distal end of the femur, after removal of the femoral prosthesis, to make holes in the femur that are arranged to accommodate the corresponding frontal positioning pins.

Preferably, the distal positioning pins are configured to smoothly engage two second centring holes arranged on a removable frontal cutting block engaged on the distal positioning pins after removal of the femoral component.

Preferably, the distal portion has a femoral centring housing configured for guiding the insertion of a bore cutter along the longitudinal axis of the femur.

Preferably, the femoral centring housing is directly formed in the distal portion.

Preferably, the femoral centring housing is formed in a femoral insert that can be removably engaged to the femoral component.

Preferably, the femoral component bears at least one attachment seat for engaging a femoral reference rod configured to indicate the orientation of the femoral component in relation to the femur's longitudinal extension.

Preferably, the distal portion is at least partially delimited in relation to the frontal portion by means of at least one femoral guide notch, which is preferably formed on a plane substantially orthogonal in relation to the longitudinal extension of the femur.

Preferably, the surgical guide also comprises a tibial component configured to exclusively couple with the proximal end of a tibia bearing a prosthetic dish attached to a tibial bone part, wherein the tibial component has:
  a front portion having a first contact area configured to act in abutment against a front cortical region of the tibial bone part;
  a proximal portion projecting in cantilever fashion on the continuation of the front portion and having at least one second contact area configured to act in abutment against a working surface of the prosthetic dish surrounded by a peripheral edge of the prosthetic dish itself;
  wherein the front portion has at least one first pair of tibial positioning holes configured to face the front cortical region of the tibia, when the tibial component is coupled with the proximal end of the tibia.

Preferably, said first contact area has an upper portion that extends according to an arched extension along the peripheral edge of the prosthetic dish.

Preferably, said first contact area has a lower portion spaced apart from the peripheral edge of the prosthetic dish.

Preferably, the tibial positioning holes belonging to the first pair are arranged spaced apart from the upper portion of the first contact area.

Preferably, the tibial positioning holes belonging to the first pair are arranged in positions spaced apart from the first contact area.

Preferably, the front portion has an additional contact area extending in an arched extension and configured to act in abutment against the prosthetic dish along the peripheral edge thereof.

Preferably, the additional contact area and the first contact area respectively extend continuously.

Preferably, the front portion has at least a second pair of tibial positioning holes, respectively aligned along a direction parallel to a first direction of mutual alignment of the tibial positioning holes belonging to the first pair.

Preferably, the front portion has at least two second pairs of tibial positioning holes, respectively aligned along a direction parallel to a direction of mutual alignment of the tibial positioning holes belonging to the first pair.

Preferably, a second distance that can be detected between the direction of mutual alignment of the tibial positioning holes belonging to the second pair and the first contact area is greater than a first distance that can be detected between the same first contact area and the direction of mutual alignment of the tibial positioning holes belonging to the first pair.

Preferably, the front portion also has at least one pair of fixing holes oriented obliquely in relation to the tibial positioning holes and configured to face the front cortical region of the tibia in positions spaced apart from the upper portion of the first contact area.

Preferably, the fixing holes are arranged at the lower portion of the first contact area.

Preferably, at least one of the first and second contact areas subtends an arc greater than 90° about a longitudinal extension axis of the tibia along the peripheral edge of the prosthetic dish.

Preferably, the proximal portion has an end edge projecting over the working surface of the prosthetic dish and extending parallel to the peripheral edge of the prosthetic dish.

Preferably, the second contact area extends along the peripheral edge of the prosthetic dish.

Preferably, the front portion has two arms projecting onto the working surface of the prosthetic dish and bearing respective terminal portions configured to act against the working surface itself at the second contact area.

Preferably, the second contact area extends along the whole extension of at least one of said arms, continuously with the first contact area.

Preferably, the proximal portion of the tibial component has a tibial centring housing configured for guiding the insertion of a bore cutter along the longitudinal axis of the tibia.

Preferably, the tibial centring housing is directly formed in the proximal portion.

Preferably, the tibial centring housing is formed in a tibial insert that can be removably engaged to the tibial component.

Preferably, the tibial component bears at least one attachment seat for attaching a tibial reference rod configured to indicate the orientation of the tibial component in relation to the tibia's longitudinal extension.

Preferably, the upper portion and the lower portion of the first contact area are at least partially separated from each other, by means of at least one tibial guide notch formed in the front portion, preferably on a plane substantially parallel to the working surface of the tibial dish.

Additional features and benefits will appear more clearly from a detailed description of a preferred, but not exclusive, embodiment of a patient-specific surgical guide to apply a total prosthetic knee revision in accordance with this invention.

This description will be set forth hereinafter with reference to the accompanying drawings—provided to illustrate rather than limit the invention's purposes—wherein.

Figure 14:
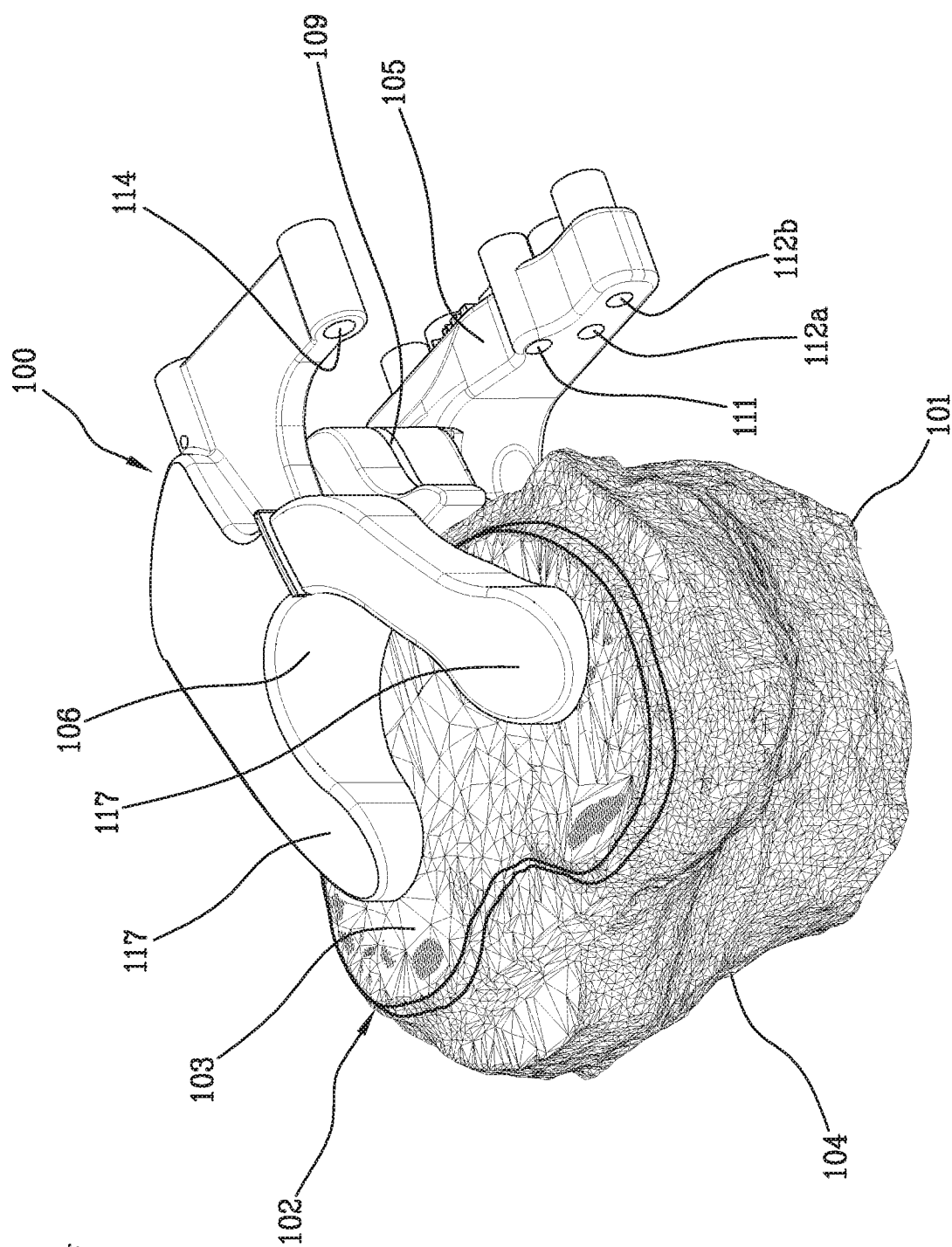
FIG. 14 shows a perspective view of the tibial component from the opposite side to FIG. 13.
Figure 15:
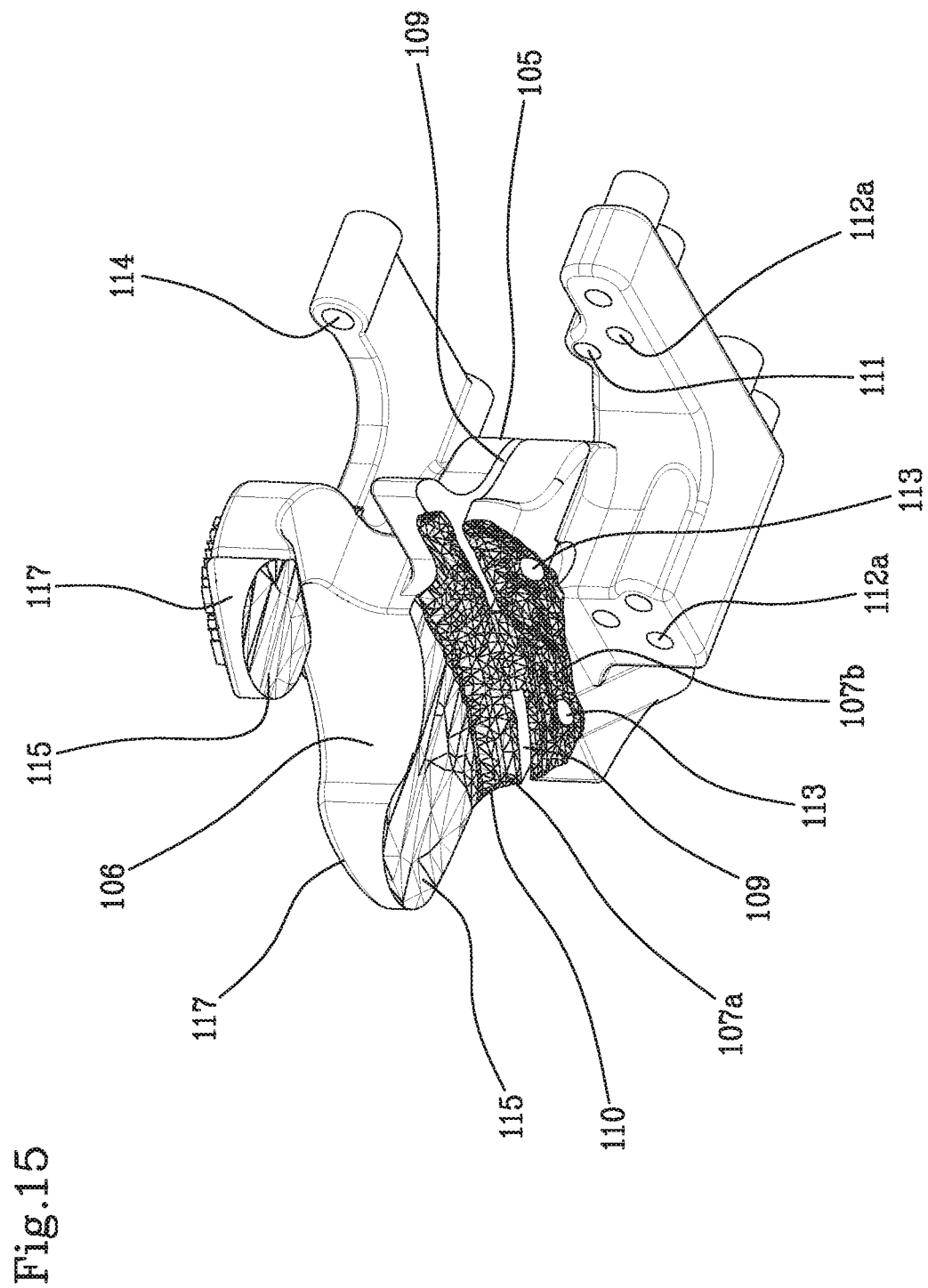
FIG. 15 is a perspective view from a different angle to FIG. 14, highlighting the tibial component in the absence of the tibia and primary tibial prosthesis.
Figure 16:
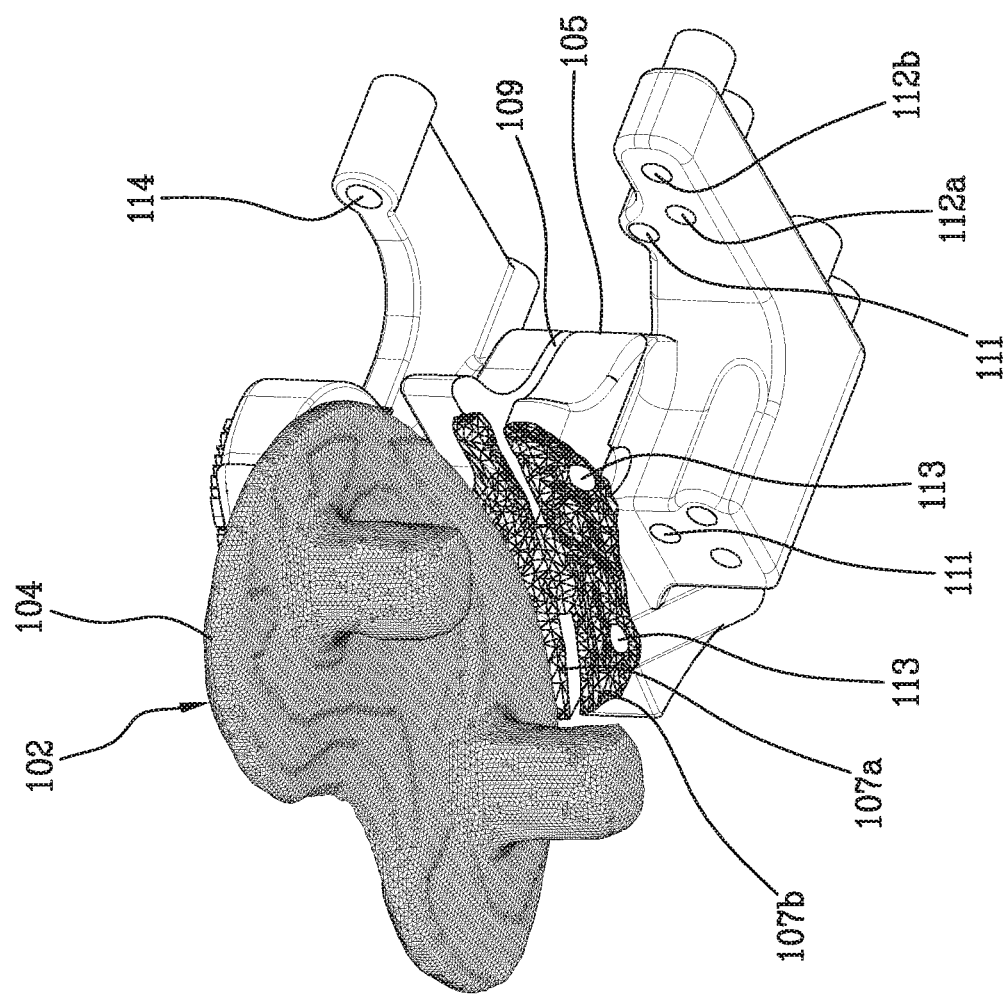

FIG. 16 is a perspective view similar to FIG. 14, in which the positioning of the tibial component in relation to the primary tibial prosthesis is also represented, in the absence of the tibial bone part; In accordance with this invention, a patient-specific surgical guide for positioning resection guides to apply a total prosthetic knee revision essentially comprises a femoral component—indicated, as a whole, with reference number 10 in FIGS. 1 to 6—and/or a tibial component—indicated, as a whole, with reference no. 100 in FIGS. 7 to 16.

For the purposes of this description, the term "patient-specific" refers to components or equipment specifically produced for use on a specific patient, based on prior surveys of the patient's bone anatomy. Since bone anatomy varies from patient to patient, a patient-specific surgical guide made for a particular patient cannot be used to perform surgery on another patient.

The femoral component 10 is configured to exclusively couple with the distal end of a femur 11 bearing a femoral prosthesis 12, also called primary femoral prosthesis, attached to a femoral bone part. The tibial component 100 is, in turn, exclusively configured to be coupled to the proximal end of a tibia 101 bearing a tibial prosthesis 112, also called a primary tibial prosthesis, attached to a tibial bone part.

For the purpose of this description, the expression "exclusively" refers to a mechanical coupling for which there is only one mutual orientation between the femoral component 10 or tibial component 100 and the patient's bone and/or prosthetic structure, so as to enable a mutual coupling when these elements are brought together in a predetermined direction. Once the coupling has taken place, mechanical bonds by mutual shape coupling ensure that the femoral component 10 or tibial component 100 and the corresponding bone structure remain permanently fixed with respect to each other in relation to any stress directed transversely or around the mutual coupling direction.

The primary femoral prosthesis 12 and the primary tibial prosthesis 112 have been implanted in the patient in a previous operation, and, in the example described here, they need to be replaced, e.g. due to wear due to prolonged use or other problems that may have arisen.

In the primary femoral prosthesis 12 a frontal region 13, which faces the front in relation to the femur 11, and a distal region 14, which faces away from the femur 11 along a longitudinal extension axis X11 of the latter, can be identified. The frontal region 13 and the distal region 14 are oriented substantially perpendicularly to each other, and mutually connected according to an arched profile as better shown in FIG. 2. The primary tibial prosthesis 112 is, in turn, substantially formed by a prosthetic dish 102 attached to the bone part of the tibia 101, and having a working surface 103 that, under operating conditions, faces the femur 11 to provide a sliding abutment seat for the femoral prosthesis 12, after the interposition of an tibial insert (not illustrated). The perimeter of the working surface 103 is delimited by a peripheral edge 104 that outlines the contour of the prosthetic dish 102.

The femoral component 10 has, essentially, a frontal portion 15 and a distal portion 16, preferably oriented transversely to each other. As better shown in FIG. 2, the frontal portion 15 and the distal portion 16 substantially extend over each other's continuation, preferably in such a way as to give the femoral component 10 an overall arched conformation on a plane containing the longitudinal axis of the femur 11.

The frontal portion 15 has a first abutment area 17 configured to act in abutment against the femoral bone part in a cortical frontal region 18 of the femur 11 and a second area 19 configured to face, preferably abutting against, a frontal region 13 of the femoral prosthesis 12, when the femoral component 10 is coupled with the distal end of the femur 11. As can be better seen in FIG. 3, the first abutment area 17 and the second area 19 can respectively extend continuously.

In the frontal portion 15, two or more guide holes 20—three in the example illustrated—are provided and oriented, respectively, according to parallel axes. These pass through the frontal portion itself so as to lead to the first abutment area 17.

In addition, at least two frontal positioning holes 21 extend through the frontal portion 15 so as to lead to the second area 19. The frontal positioning holes 21 are each positioned between at least one of the guide holes 20 and the distal portion 16, and are preferably oriented according to respective axes substantially parallel to the guide holes 20. Preferably, the frontal positioning holes 21 are oriented according to respective axes substantially perpendicular to a longitudinal extension direction of the femur 11, i.e. to the longitudinal axis X11, when the femoral component 10 is coupled to the distal end of the femur 11.

Preferably, one or more attachment seats 22 for engaging a femoral reference rod (not illustrated) configured to indicate the orientation of the femoral component 10 in relation to the femur's longitudinal extension 11 are provided, preferably in the frontal portion 15.

Preferably, the femoral component 10 also has two lateral abutments 23 bearing third abutment areas 24 configured to act in abutment against the femoral bone part in medial and lateral epicondylar regions, respectively, of the femur 11. More specifically, the lateral abutments 23 are borne at the end by corresponding brackets 25 protruding from opposite sides respectively of the distal portion 16, and have corresponding auxiliary positioning holes 26 extending through the third abutment areas 24, preferably according to respectively converging axes.

The distal portion 16 is, in turn, configured to face the distal end of the femur 11, and preferably has at least a fourth abutment area 27, preferably arranged in a substantially orthogonal orientation in relation to the first abutment area 17, and configured to act in abutment against the distal region 14 of the femoral prosthesis 12. Preferably, the fourth abutment area 27 is divided into two portions arranged in corresponding condylar zones.

The distal portion 16 bears at least two distal positioning holes 28, 29, preferably oriented along their respective axes substantially parallel to a longitudinal extension direction of the femur 11. In the example illustrated, a first pair of distal positioning holes 28 and a second pair of distal positioning holes 28, arranged at different distances from the frontal portion 15, are provided. When the femoral component 10 is coupled to the distal end of the femur 11, the distal positioning holes 28, 29 face the distal region 14 of the femoral prosthesis 12.

One or more femoral guide notches 30 formed on a substantially parallel plane orthogonal in relation to the longitudinal extension of the femur 11, at least partially delimit the distal portion 16 from the frontal portion 15.

The femoral guide notches 30 can, advantageously, be used for guiding cutting tools and/or for engaging one or more reference plates, not illustrated as they are known, that make it possible to highlight for the surgeon the position and orientation of the plane according to which a distal resection cut must be performed on the femoral bone.

The distal portion 16 may have a femoral centring housing 31, e.g. in the form of a hole or circular profile sleeve, configured to guide the insertion of a bore cutter along the longitudinal axis of the femur 11.

Figure 1:
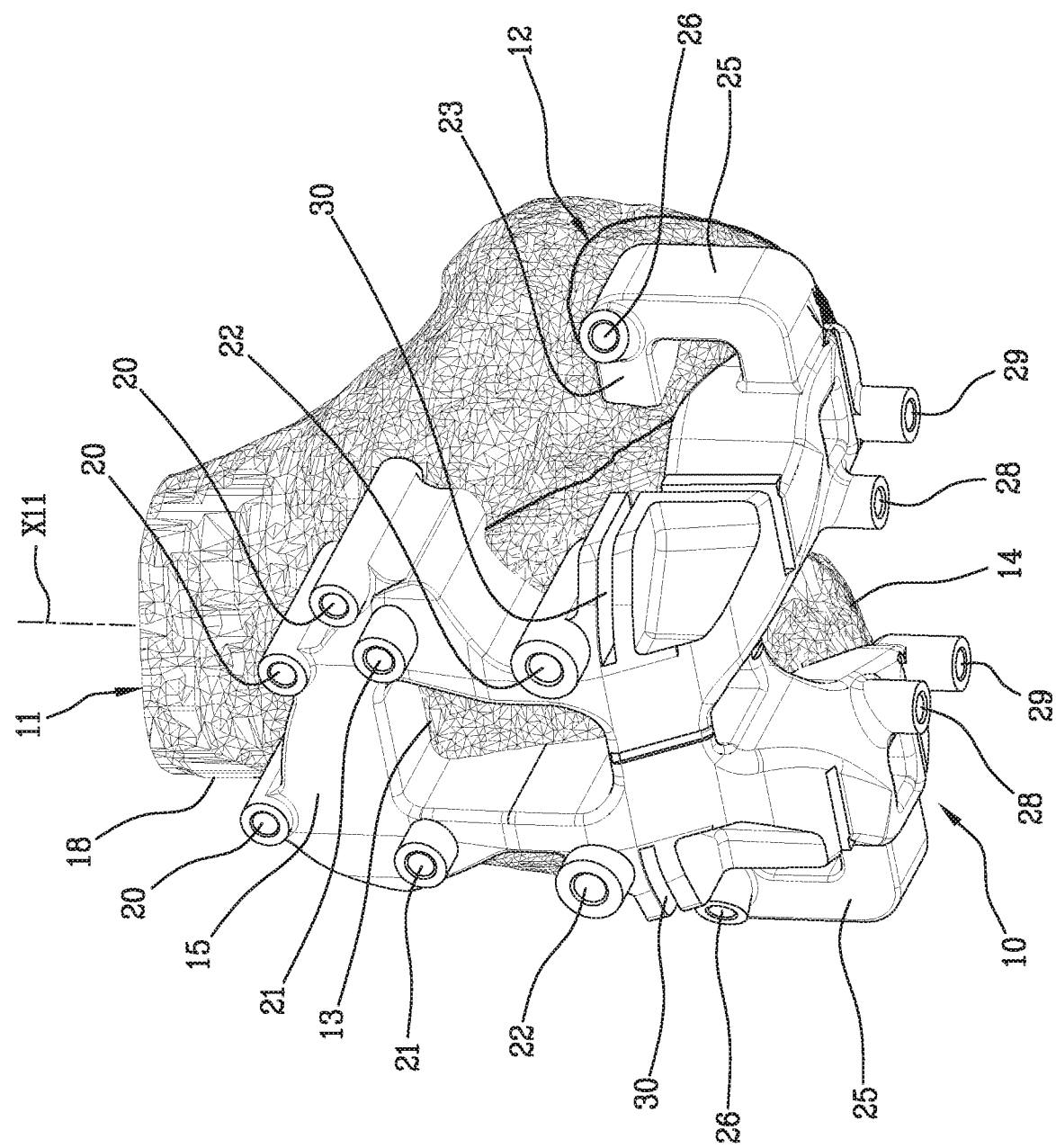
FIG. 1 shows in frontal perspective view a femoral component of a surgical guide according to the invention, applied to the distal end of a femur bearing a primary prosthesis.
Figure 2:
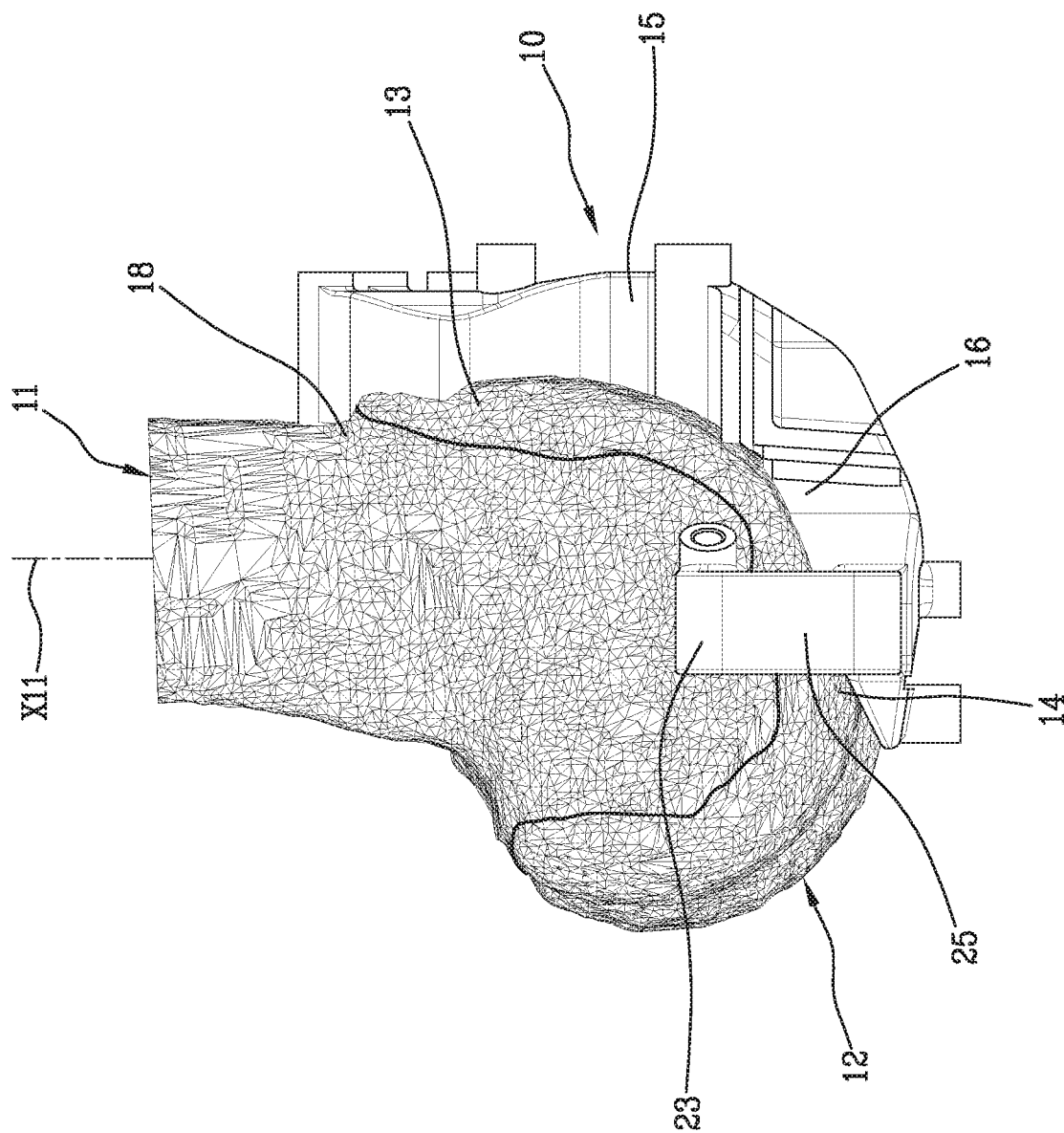
FIG. 2 shows a side view of the femoral component in FIG. 1.
Figure 3:
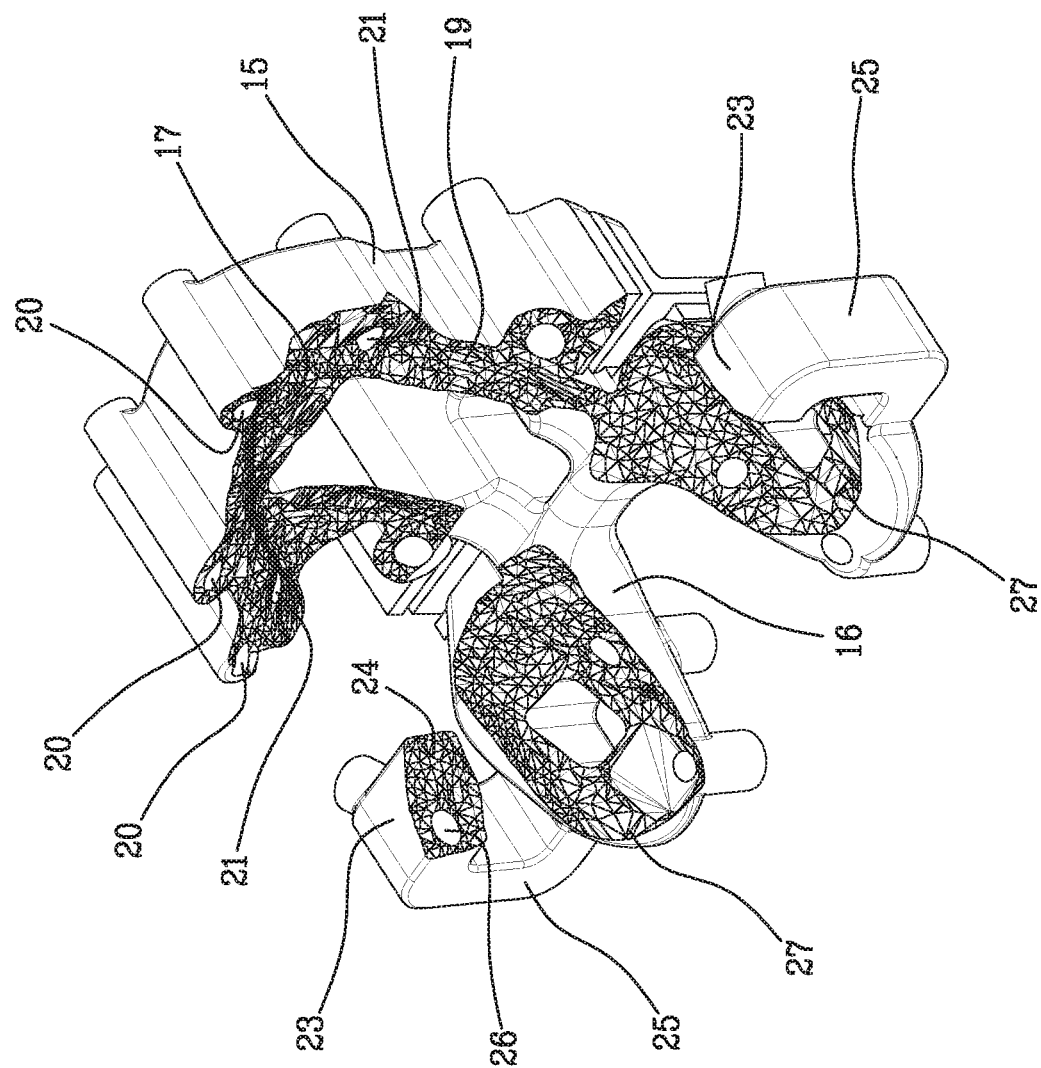
FIG. 3 shows a perspective view from the opposite side in relation to FIG. 1, highlighting the femoral component in the absence of the femur and primary prosthesis.
Figure 4:
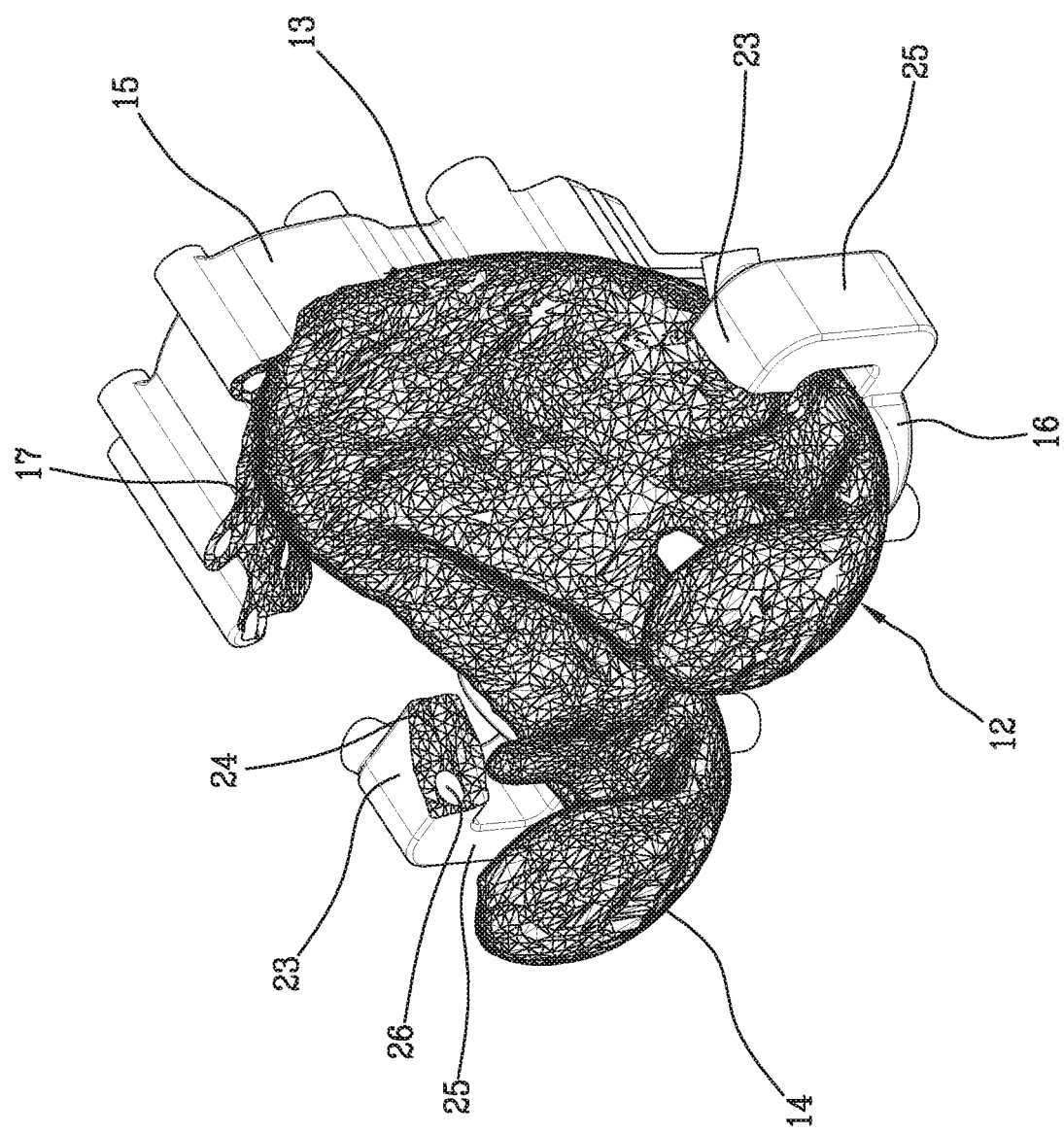
FIG. 4 is a perspective view similar to FIG. 3, in which the positioning of the femoral component in relation to the primary prosthesis is also represented, in the absence of the femoral bone part.
Figure 5:
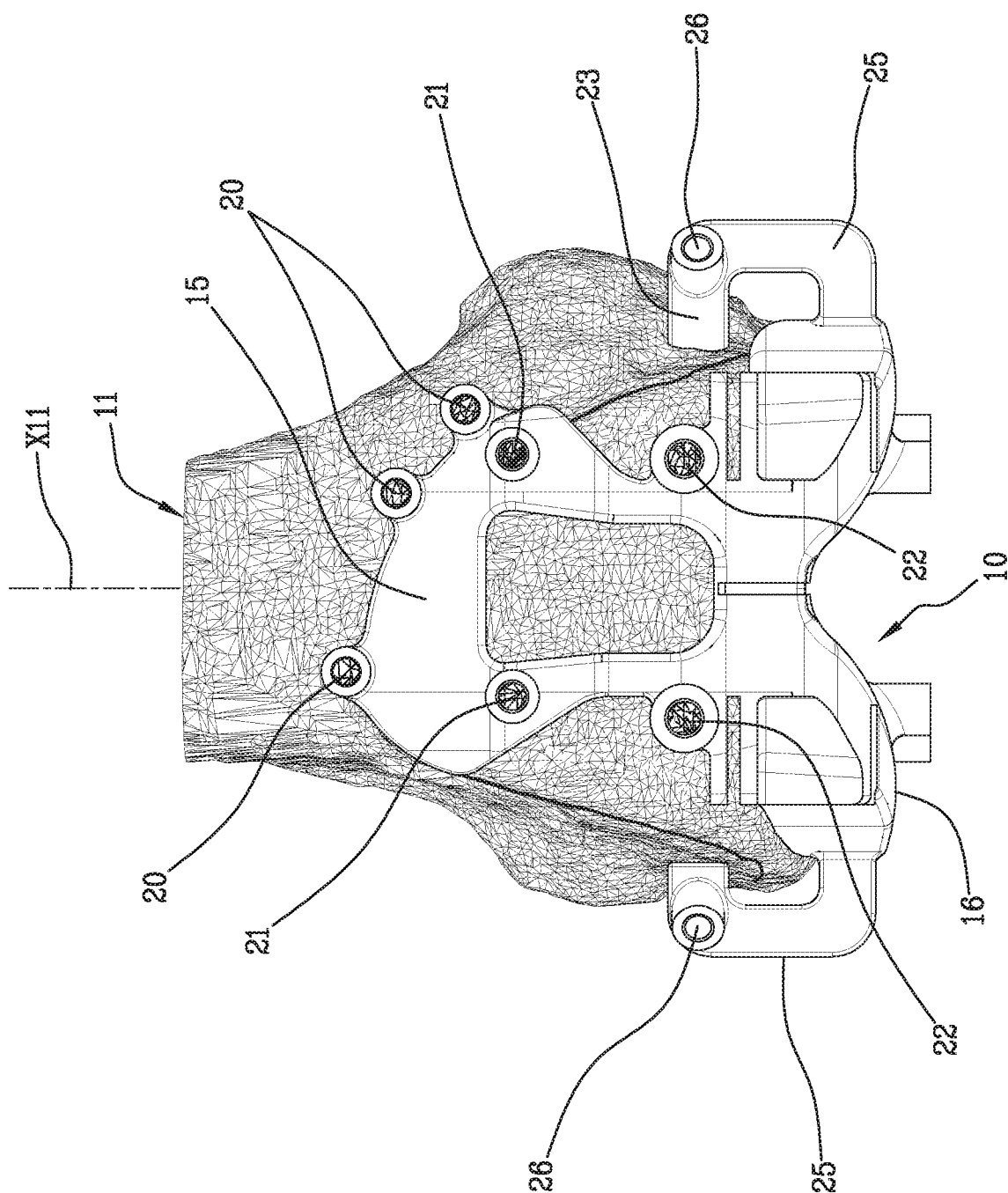
FIG. 5 is a frontal view of the femoral component applied to the distal end of the femur.
Figure 6:
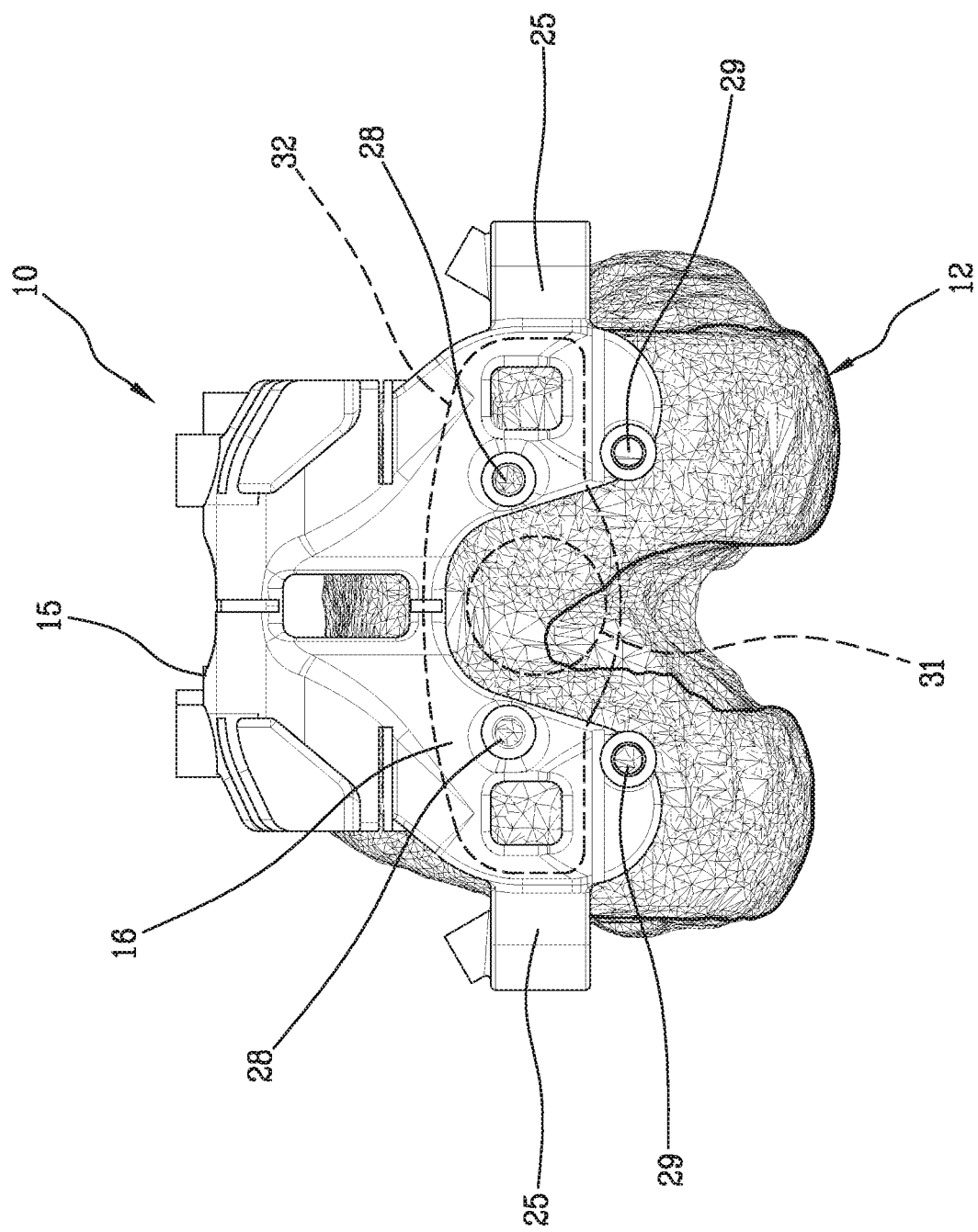
FIG. 6 shows the femoral component from a distal direction of the femur.
Figure 7:
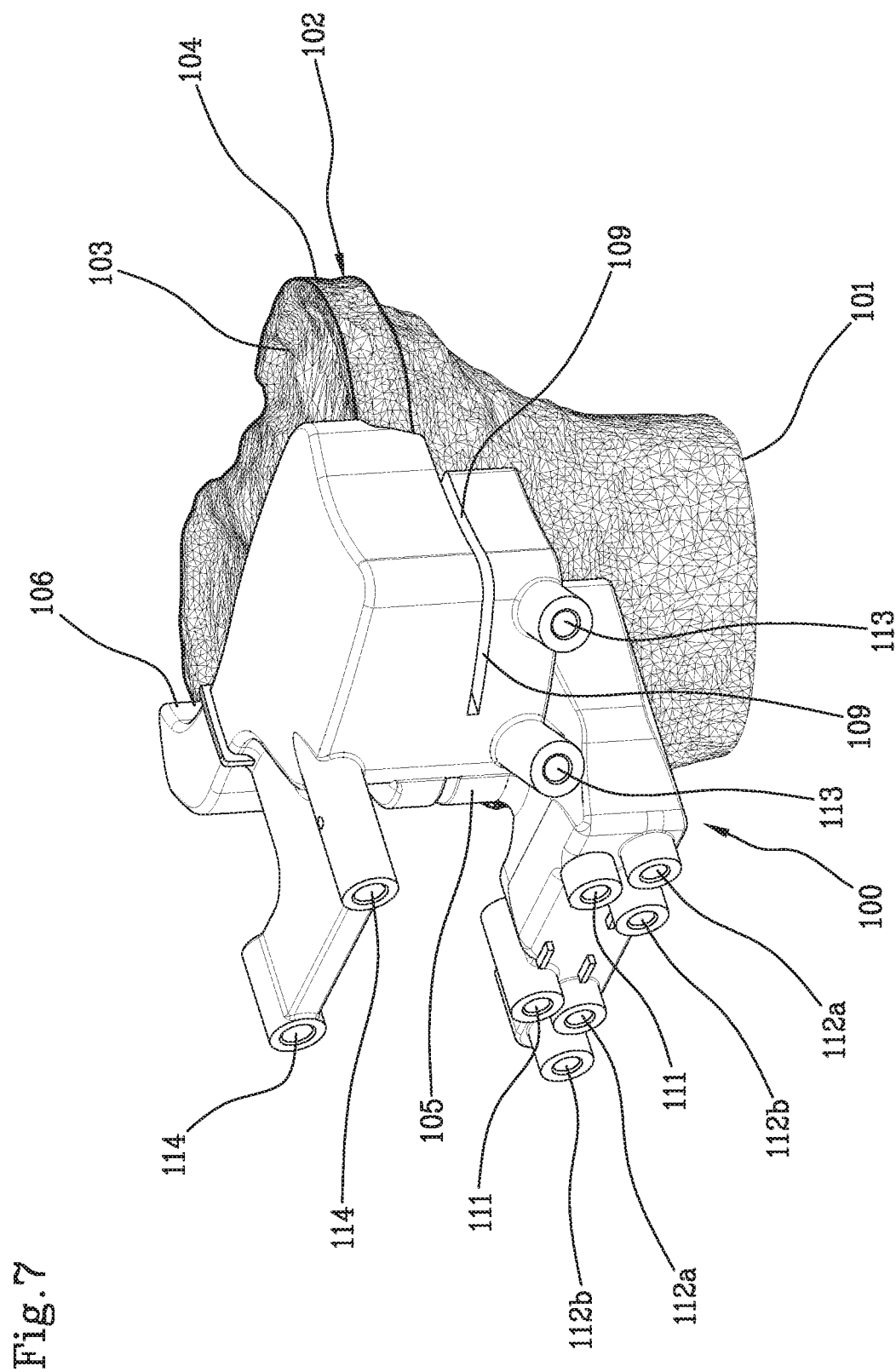
FIG. 7 shows in frontal perspective view a first embodiment of a tibial component of the surgical guide according to the invention, applied to the proximal end of a tibia bearing a primary tibial prosthesis.
Figure 8:
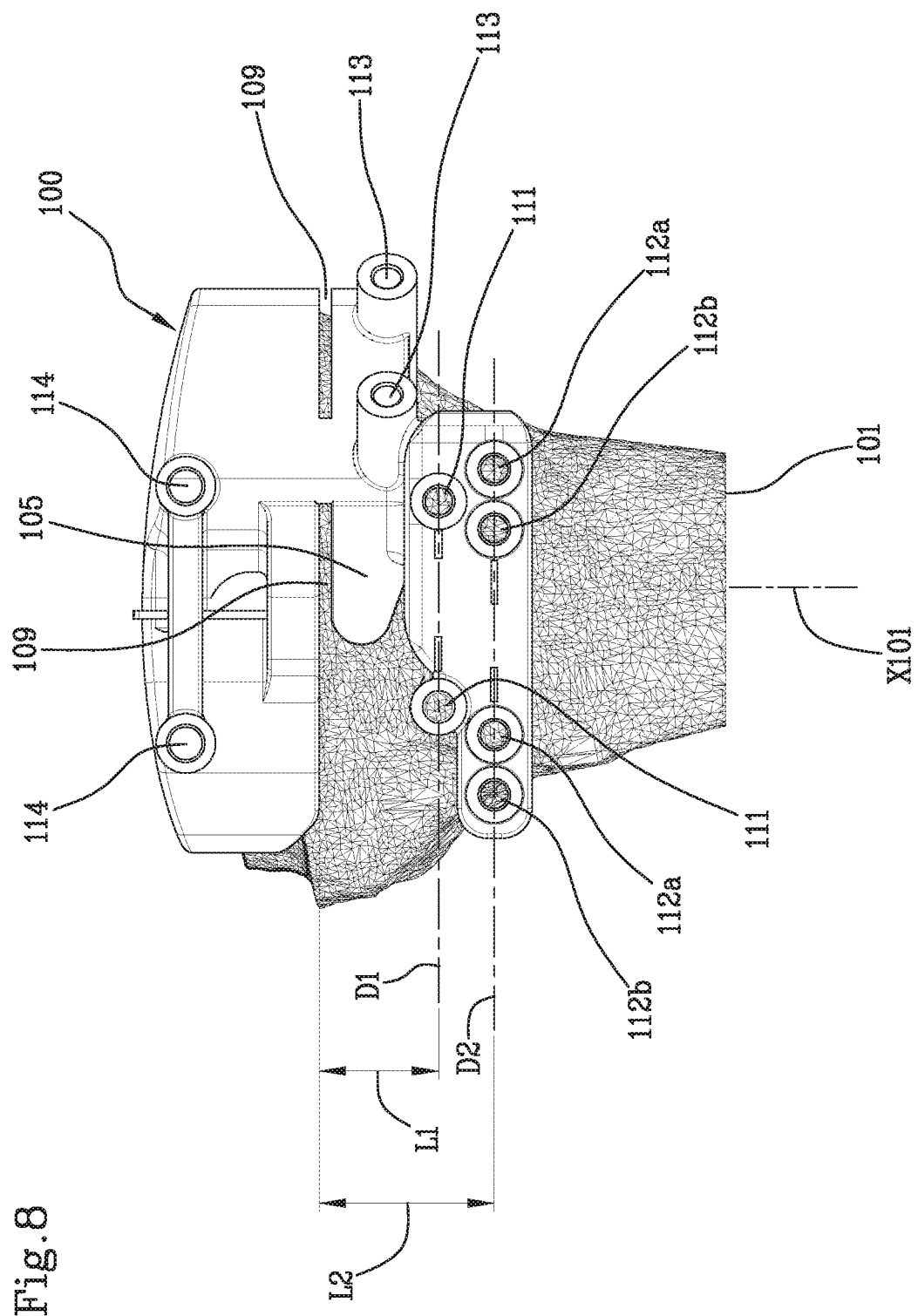
FIG. 8 shows a frontal view of the tibial component in FIG. 7.
Figure 9:
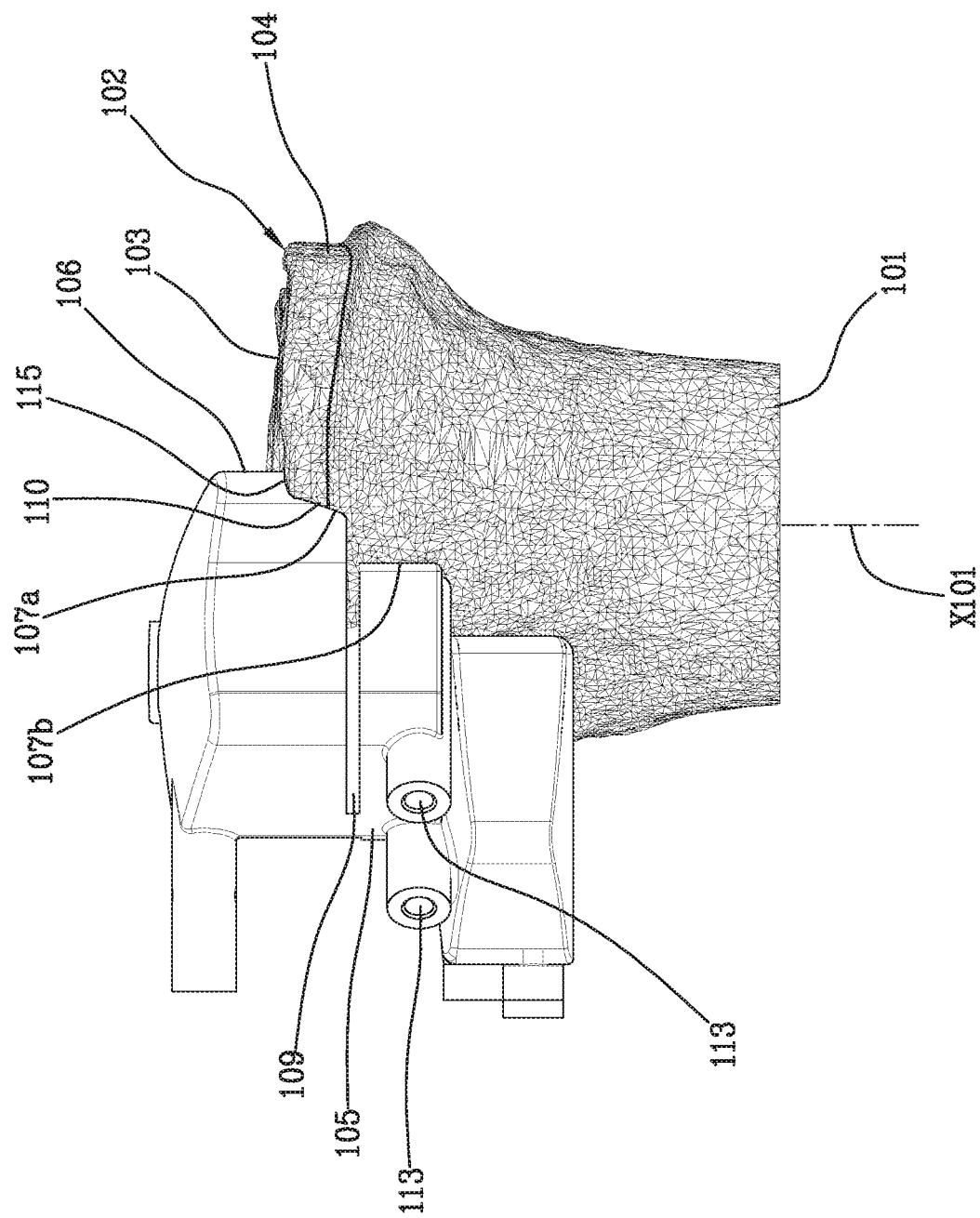
FIG. 9 shows a lateral view of the tibial component in FIG. 7.
Figure 10:
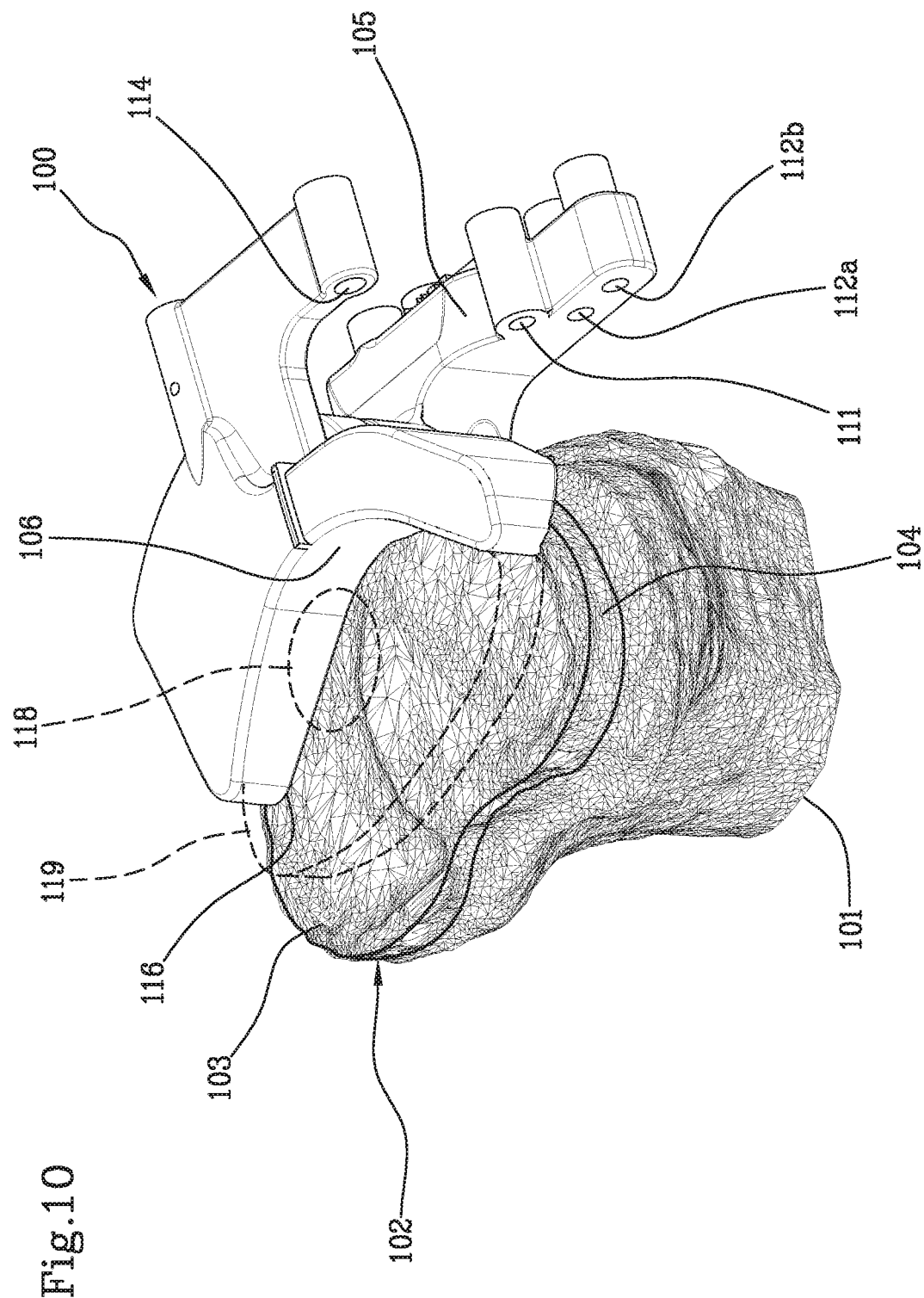
FIG. 10 shows a perspective view of the tibial component from the opposite side in relation to FIG. 7.
Figure 11:
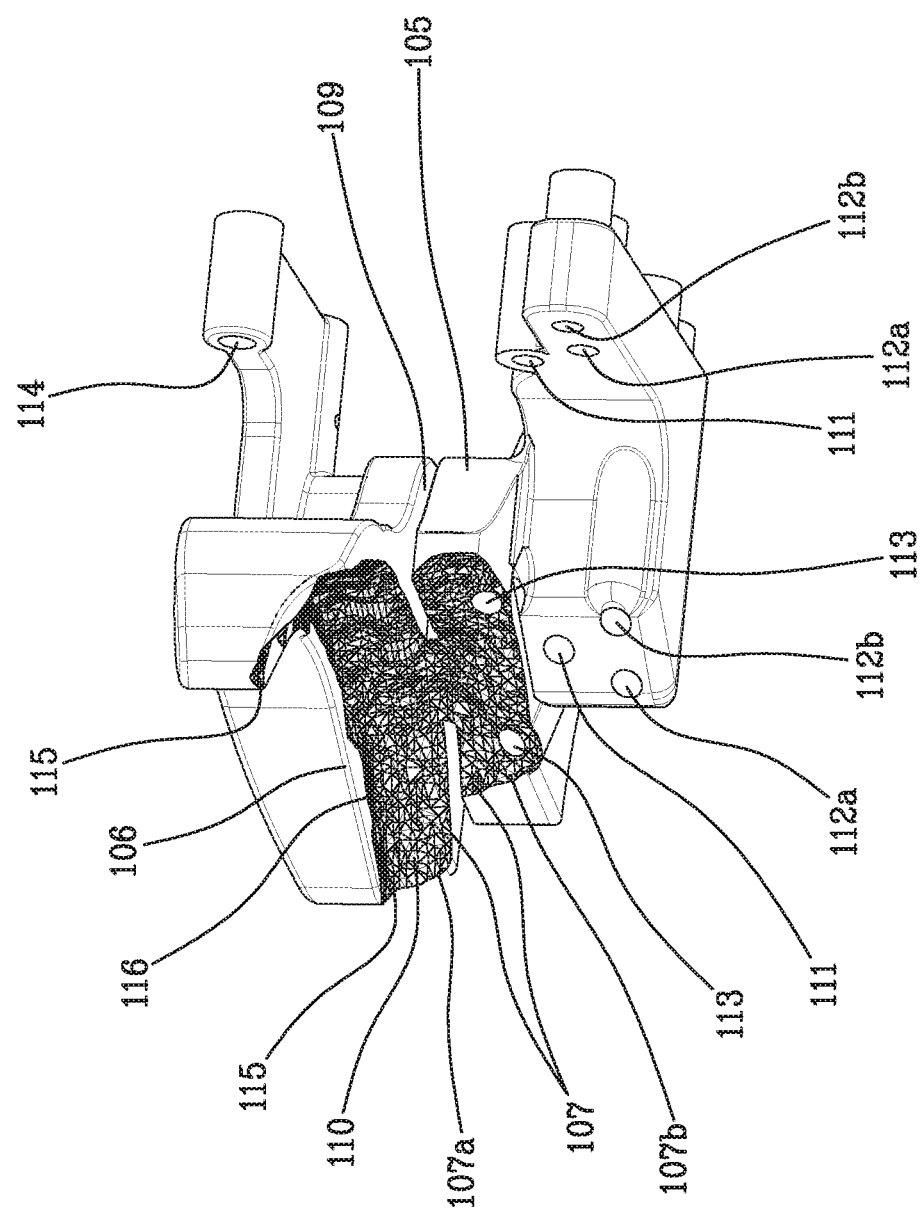
FIG. 11 is a perspective view from a different angle to FIG. 10, highlighting the tibial component in the absence of the tibia and primary tibial prosthesis.
Figure 12:
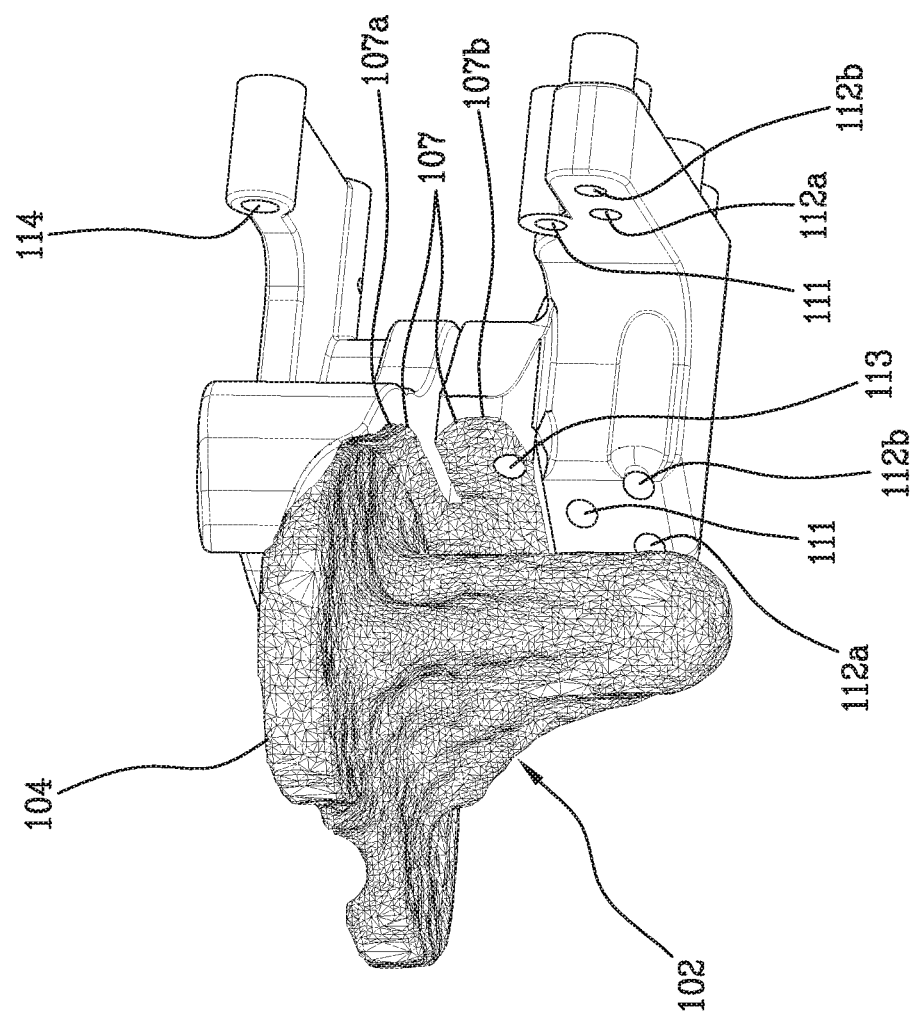
FIG. 12 is a perspective view similar to FIG. 11, in which the positioning of the tibial component in relation to the primary tibial prosthesis is also represented, in the absence of the tibial bone part.
Figure 13:
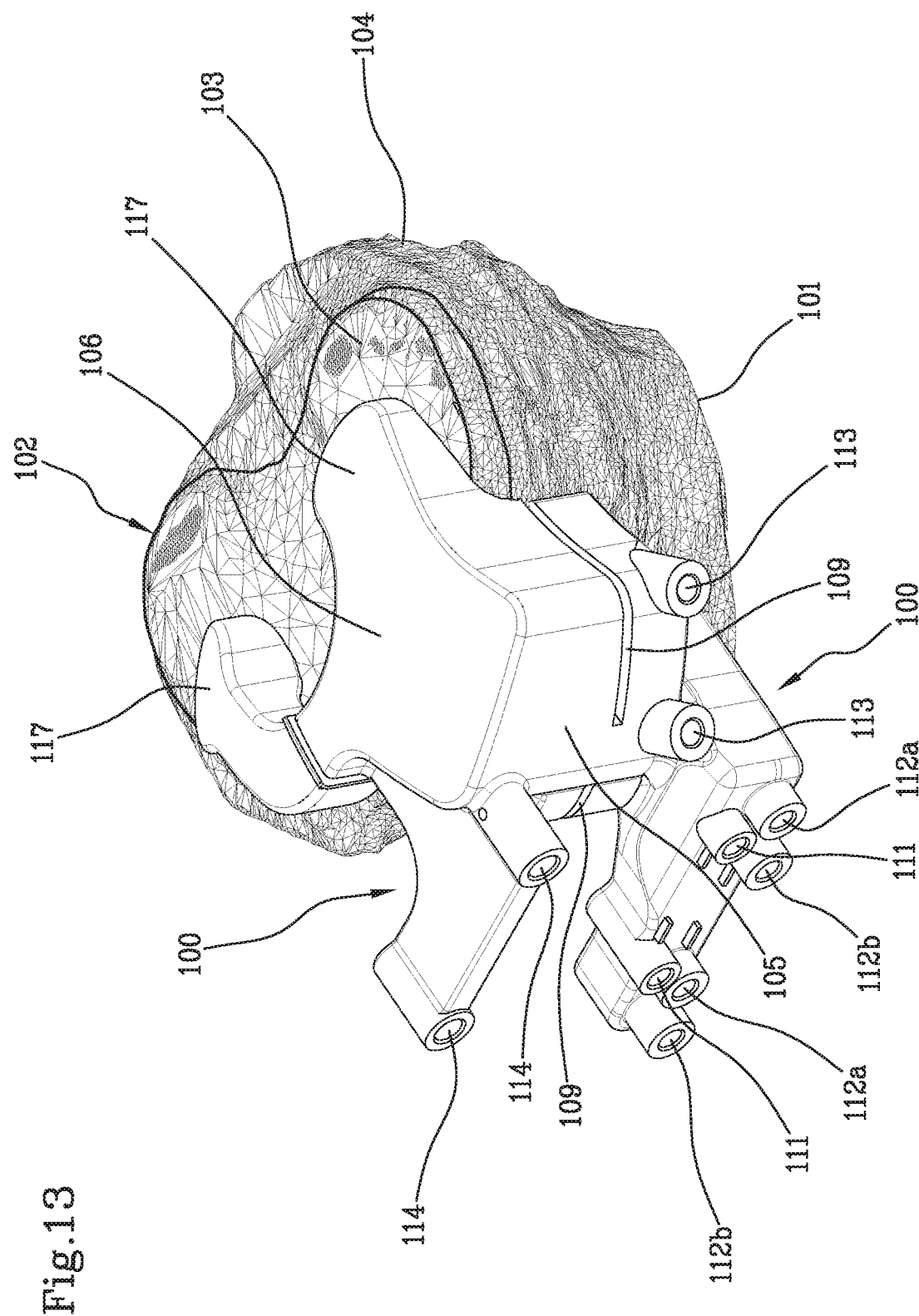
FIG. 13 shows in frontal perspective view a second embodiment of a tibial component of the surgical guide according to the invention, applied to the proximal end of a tibia bearing a primary tibial prosthesis.

The femoral centring housing 31 can be directly formed in the distal portion 16, or borne by a femoral insert 32, which can be removably engaged to the femoral component 10, as schematically shown in dashed lines in FIG. 6.

In the tibial component 100 a front portion 105 and a proximal portion 106, projecting in cantilever fashion onto the continuation of the front portion 105, can be identified.

The front portion 105 has a first contact area 107 configured act in abutment against a front cortical region 108 of the tibial bone part 101, when the tibial component 100 is coupled with the proximal end of the tibia. Preferably, as better shown in FIGS. 12 and 16, in the first contact area 107, an upper portion 107a, which extends in an arched extension parallel to the extension of the adjacent peripheral edge 104 of the prosthetic dish 102, and a lower portion 107b, which is spaced apart from the peripheral edge 104 of the prosthetic dish 102, can be identified.

At least at the upper portion 107a, the first contact area 107 has an extension sufficient to subtend an arc greater than 90° along the peripheral edge 104 of the prosthetic dish 102 and around the longitudinal extension axis of the tibia. In the attached figures, the longitudinal extension of the tibia 101 is represented by the longitudinal axis X101.

One or more tibial guide notches 109 formed in the front portion 105 on a plane substantially parallel to the working surface 103 of the tibial dish 102, separate, at least partially, the upper portion 107a from the lower portion 107b of the first contact area 107. The tibial guide notches 109 can, advantageously, be used for guiding cutting tools and/or for engaging one or more reference plates, not illustrated as they are known, that make it possible to highlight for the surgeon the position and orientation of the plane according to which a frontal resection cut must be performed on the femoral bone part.

Preferably, the front portion 105 also has an additional contact area 110 (FIGS. 11 and 15), extending in mutual continuity with the first contact area 107, according to an arched extension. The additional contact area 110 is configured to act directly in abutment against the prosthetic dish 102 along the peripheral edge 104 of the dish, approximately in an area bound between the lying plane of the working surface 103 and a plane containing the lower edge of the prosthetic dish.

At least one first pair of tibial positioning holes 111, configured to face the front cortical region 108 of the tibia 101 when the tibial component 100 is coupled with the proximal end of the tibia, is provided in the front portion 105.

The tibial positioning holes 111 are preferably arranged in positions spaced apart from the first contact area 107 or at least from the upper portion 107a of the latter. More specifically, the geometrical axes of the tibial positioning holes 111 belonging to the first pair are respectively aligned along a first alignment direction D1 substantially parallel to the lying plane of the working surface 103 of the tibial dish 102, at a first distance L1 from the first contact area 107.

There may also be at least one second pair of tibial positioning holes 112a, 112b, respectively aligned with their geometrical axes along a second alignment direction D2 parallel to the first alignment direction D1. In a preferred embodiment there are two second pairs of tibial positioning holes, respectively indicated with 112a and 112b, parallel to each other and aligned along the second alignment direction D2. The second alignment direction D2 is arranged, in relation to the first contact area 107, at a second distance L2 greater than the first distance L1.

The front portion 105 of the tibial component 100 also has at least one pair of fixing holes 113, oriented obliquely in relation to the tibial positioning holes 111, 112a, 112b and configured to face the front cortical region 108 of the tibia 101 in positions spaced apart from the upper portion 107a of the first contact area 107.

Preferably, as can be seen in FIGS. 11, 12, 15, and 16, the fixing holes 113 are arranged at the lower portion 107b of the first contact area 107. The tibial component 100 also has, preferably on the front portion 105, at least one engagement seat 114 for attaching a tibial reference rod (not illustrated) configured to indicate the orientation of the tibial component 100 in relation to the tibia's longitudinal extension.

In the embodiments respectively represented in FIGS. 7 to 12 and 13 to 16, the proximal portion 106 has a different conformation respectively, but in both cases it comprises at least one second contact area 115, configured to act in abutment against the working surface 103 circumscribed by the peripheral edge 104 of the prosthetic dish 102.

More specifically, in the embodiments in FIGS. 7 to 12, the proximal portion 106 has an end edge 116 projecting onto the working surface 103 of the prosthetic dish 102, and extending parallel to the peripheral edge 104 of the prosthetic dish 102 itself. In this case the second contact area 115 extends substantially against the peripheral edge 104 of the prosthetic dish 102, along the peripheral extension of the same, preferably widely enough to subtend an arc greater than 90° about the longitudinal development axis of the tibia. This configuration is particularly suitable for use on tibial prostheses of the "fixed insert" type. In this type of prosthesis a fixed insert (not illustrated) can be provided, which will be positioned between the tibial dish 102 and the femoral prosthesis 12 in its operating condition without the possibility of its sliding onto the working surface 103. In the embodiment shown in FIGS. 13 to 16, the second contact area 115 is formed on two arms 117 projecting onto the working surface 103 of the prosthetic dish 102. The arms 117 have corresponding terminal portions configured to act in abutment against the working surface 103 itself at the second contact area 115. Preferably, as shown in FIG. 15, in at least one of the arms 117 the second contact area 115 occupies the entire extension of the arm itself, continuously connecting with the first contact area 107.

This configuration is particularly suitable for use on tibial prostheses of the "movable insert" type. In this type of prosthesis, a movable insert (not illustrated) is provided, which will be positioned between the tibial dish 102 and the femoral prosthesis 12 in its operating condition with some freedom to slide onto the working surface 103.

The proximal portion 106 may have a tibial centring housing 118, e.g. in the form of a hole or circular profile sleeve, configured to guide the insertion of a bore cutter along the longitudinal axis X101 of the tibia 101. The tibial centring housing 118 can be directly formed in the proximal portion 106, or borne by a tibial insert 119, which can be removably engaged to the tibial component 100, as shown in dashed lines in FIG. 10.

Performing prosthetic revision surgery in accordance with this invention requires that the patient-specific surgical guide, structured as described above, is produced in a pre-operative planning phase. More specifically, the production of the surgical guide 10, 100 requires that the patient undergo radiography, computed tomography, magnetic resonance imaging, or another suitable detection method, to detect the anatomical conformation of the distal end of the femur 11 and the proximal end of the tibia 101. As a result of this survey, a mathematical model representative of the anatomical configuration of the distal end of the femur 11 and the proximal end of the tibia 101, including the primary, femoral 12 and tibial 102 prostheses previously implanted in the patient, will be obtained by means of electronic image processing and/or other acquired data. The mathematical model is then used to model, by means of mechanical processing and/or a 3D printing process, the abutment areas 17, 19, 24, 27 of the femoral component 10 and the contact areas 107, 110, 115 of the tibial component 100, so as to obtain the patient-specific surgical guide in which these areas are conformed so as to reproduce, in negative, the shape of the bone and/or prosthetic parts against which they must come into contact.

Once the femoral component 10 and the tibial component 100 have been created, the surgeon cuts the patient's epidermis and soft tissue until the knee of the patient to be operated on is exposed.

The femoral component 10 is positioned on the distal end of the femur 11 bearing the femoral prosthesis 12. In this circumstance, the combined action of the first 17, second 19, third 24, and/or fourth 27 abutment areas acting on both the surfaces of the bone part and the femoral prosthesis 12, determines an exclusive and stable coupling between the femoral component 10 and the distal end of the femur 11.

Corresponding alignment pins (not illustrated) are introduced along at least two of the guide holes 20, the pins also being firmly inserted through the frontal cortical region 18 of the femur 11. Each of the guide holes 12 is suitable for guiding the corresponding alignment pin through the femoral bone part, in a position spaced apart from the peripheral edge of the femoral prosthesis 12. It can be arranged that, before the alignment pins are inserted, corresponding holes are drilled in the frontal cortical region 18 of the femur 11 by means of a drill bit or other drilling tool guided through the corresponding guide holes 20.

The femoral component 10 can then be removed from the guide pins and removed from the distal end of the femur 11 to allow subsequent removal of the primary femoral prosthesis 12 that needs to be replaced.

After removal, the femoral component 10 is repositioned by re-fitting the guide holes 20 along the positioning pins, the reciprocal engagement of which ensures that, despite the absence of the femoral prosthesis 12, the femoral component 10 and the distal end of the femur 11 are re-engaged, exclusively and firmly, exactly in the exclusive engagement position previously assumed.

The correct positioning of the femoral component 10 can also be visually checked by means of the reference plates that can be inserted into the femoral guide notches 30, and/or by means of the reference rod that can be inserted into the attachment seats 22.

Two fixing pins that can be inserted, after any drilling, in the epicondylar regions through the auxiliary positioning holes 26, can be used to additionally stabilise the positioning of the femoral component 10.

Two pairs of frontal attachment holes are then drilled in the condylar areas of the bone part, using a drill bit guided through the frontal positioning holes 21 and through the first or second pair of distal positioning holes 28, 29. The femoral component 10 positioned on the distal end of the femur 11 can also be used to guide a drilling and/or milling tool through the femoral centring housing 31 to prepare the medullary canal of the femur 11 to receive a new femoral revision prosthesis. The finishing direction of the canal can therefore be guided according to the tilt of the distal resection cut of the femur 11 planned in the pre-operative phase.

Once the operations described above have been completed, the femoral component 10 and the guide pins can be removed.

A pair of frontal positioning pins and a pair of distal positioning pins (not illustrated) are inserted into the holes made through the frontal guide holes 20 and the distal guide holes 20 respectively.

Once attached, the frontal positioning pins are suitable for smoothly engaging two first centring holes arranged on a distal cutting block, which is positioned against the bone part and used, in a known way, to guide the execution of a distal resection cut on the distal end of the femur 11. The tilt of the distal resection is given by the position of the positioning pins based on pre-operative planning.

Similarly, the distal positioning pins are suitable for smoothly engaging two second centring holes arranged on a frontal cutting block, which is positioned against the bone part and used, in a known way, to guide the execution of frontal, posterior, and beveling resection cuts on the distal end of the femur 11.

The choice of using the first or second pair of distal positioning holes 28, 29 for operating purposes can be determined by the type of frontal cutting block the surgeon plans to use for subsequent resections. If the use of a frontal cutting block identical to the one previously used for implanting the primary prosthesis is planned, the distal positioning holes 28 belonging to the first pair will be used. If, on the other hand, the surgeon plans to use a different block from the one previously used for implanting the primary prosthesis, so that a revision resection can be performed in a different position from the resection performed during the attaching of the primary femoral prosthesis 12, the distal positioning holes 29 belonging to the second pair can be used.

After the resection cuts have been made, the new revision femoral prosthesis can be attached after the removal of the positioning pins.

The surgery on the tibia 101 involves positioning the tibial component 100 on the proximal end of the tibia after removal of the tibial insert from the primary tibial prosthesis 112. In this circumstance, the combined action of the abutment areas acting on both the surfaces of the bone part and the surfaces of the primary tibial prosthesis 112, determines the exclusive and firm engagement of the tibial component 100 on the proximal end of the tibia 101.

In at least one of the pairs of tibial positioning holes 111, 112a, 112b, the corresponding tibial positioning pins are inserted through the frontal cortical region 18 of the tibia 101 after any drilling through the same tibial positioning holes.

The correct positioning of the tibial component 100 can also be visually checked by means of the reference plates that can be inserted into the tibial guide notches 109, and/or by means of the reference rod that can be inserted into corresponding the engagement seats 22.

The tibial component 100 positioned on the proximal end of the tibia 101 can also be used to guide a drilling and/or milling tool through the tibial centring housing 118 to prepare the medullary canal of the tibia to receive a new revision tibial prosthesis. The finishing direction of the canal can therefore be guided according to the tilt of the tibial resection cut planned in the pre-operative phase.

The tibial component 100 can then be removed from the tibial positioning pins and removed from the proximal end of the tibia 101 to allow subsequent removal of the primary tibial prosthesis 112 that needs to be replaced.

Once removed, the tibial positioning pins are suitable for smoothly engaging corresponding centring holes arranged on a tibial cutting block, which is positioned against the bone part and used, in a known way, to guide the execution of a tibial resection cut on the proximal end of the tibia 101.

The choice of using the first or second pair of the tibial positioning holes for installing the tibial positioning holes can be determined by the type of tibial cutting block the surgeon plans to use for subsequent tibial resections. Should a tibial cutting block identical to the one previously used for implanting the primary tibial prosthesis 112 be used, the distal positioning holes 111 belonging to the first pair will be used. Should a different block from the one previously used for implanting the primary prosthesis be used for the purpose of performing a revision tibial resection, the tibial positioning holes 112a, 112b belonging to the second pairs may be used. The choice of either one or the other second pair of tibial holes 112a, 112b can also be planned in the pre-operative phase so as to avoid interference with the primary prosthesis.

After the tibial resection cuts have been made, the new revision tibial prosthesis can be attached after the removal of the tibial positioning pins.

The invention claimed is:

1. A patient-specific surgical guide to apply a total prosthetic knee revision, comprising:
    a femoral component configured to exclusively couple with a distal end of a femur bearing a femoral prosthesis attached to a femoral bone;
    wherein the femoral component has:
        a distal portion configured to face the distal end of the femur, bearing at least two distal positioning holes configured to face a distal region of the femoral prosthesis when the femoral component is coupled with the distal end of the femur; and
        a first bracket extending from a first side of the distal portion and a second bracket extending from a second side of the distal portion, wherein the first and second sides are opposite each other relative to a longitudinal axis of the distal portion,
    wherein a lateral abutment extends from each bracket in a direction toward the longitudinal axis of the distal portion, and each lateral abutment terminates at a third abutment area that is configured to abut epicondylar regions of the femoral bone;
        a frontal portion extending on a continuation of the distal portion and displaying a first abutment area configured to act in abutment against a femur bone part in a cortical frontal region of the femur, and a second area configured to face a frontal region of the femoral prosthesis, when the femoral component is coupled with the distal end of the femur;
    wherein the frontal portion defines:
        at least two guide holes, extending parallel to each other through the frontal portion at the first abutment area; and
        at least two frontal positioning holes extending through the frontal portion at the second area.

2. The surgical guide according to claim 1, wherein each lateral abutment defines an auxiliary positioning hole extending through the third abutment area.

3. The surgical guide according to claim 1, wherein the second area is configured to act in abutment against the frontal region of the femoral prosthesis.

4. The surgical guide according to claim 1, wherein the distal portion has at least a fourth abutment area configured to act in abutment against the distal region of the femoral prosthesis.

5. The surgical guide according to claim 1, wherein the guide holes are configured to slidably engage respective alignment pins that can be inserted through the frontal cortical region of the femur.

6. The surgical guide according to claim 1, wherein the frontal positioning holes are oriented according to respective axes parallel to the guide holes.

7. The surgical guide according to claim 1, wherein the frontal positioning holes are configured to slidably engage a drilling tool that can be inserted through the femoral bone part when the femoral component is coupled with the distal end of the femur after removing the femoral prosthesis.

8. The surgical guide according to claim 1, wherein the distal positioning holes are oriented according to respective axes parallel to a longitudinal extension direction of the femur when the femoral component is coupled with the distal end of the femur.

9. The surgical guide according to claim 1, wherein the distal positioning holes are configured to slidably engage of a drilling tool that can be inserted through the femoral bone part when the femoral component is coupled with the distal end of the femur after removing the femoral prosthesis.

10. The surgical guide according to claim 1, wherein the distal portion has a femoral centering housing configured for guiding insertion of a bore cutter along the longitudinal axis of the femur.

11. The surgical guide according to claim 10, wherein the femoral centering housing is directly formed in the distal portion.

12. The surgical guide according to claim 10, wherein the femoral centering housing is formed in a femoral insert that can be removably engaged to the femoral component.

13. The surgical guide according to claim 1, wherein the distal portion is at least partially delimited with respect to the frontal portion by means of at least one femoral guide notch.

14. The surgical guide according to claim 1, further comprising a tibial component configured to exclusively couple with a proximal end of a tibia bearing a prosthetic dish attached to a tibial bone part;
    wherein the tibial component has:
        a front portion having a first contact area configured to act in abutment against a front cortical region of the tibial bone part;
        a proximal portion projecting in cantilever fashion on a continuation of the front portion and having at least one second contact area configured to act in abutment against a working surface of the prosthetic dish surrounded by a peripheral edge of the prosthetic dish itself;
    wherein the front portion has at least one first pair of tibial positioning holes configured to face the front cortical region of the tibia, when the tibial component is coupled with the proximal end of the tibia.

15. The surgical guide according to claim 14, wherein said first contact area has an upper portion that extends according to an arched extension along the peripheral edge of the prosthetic dish.

16. The surgical guide according to claim 15, wherein said first contact area has a lower portion spaced apart from the peripheral edge of the prosthetic dish.

17. The surgical guide according to claim 16, wherein the upper portion and the lower portion of the first contact area are at least partially separated from each other, by means of at least one tibial guide notch formed in the front portion.

18. The surgical guide according to claim 15, wherein the tibial positioning holes belonging to the first pair are arranged in positions spaced apart from the upper portion of the first contact area.

19. The surgical guide according to claim 15, wherein the frontal portion also has at least one pair of fixing holes oriented obliquely with respect to the tibial positioning holes and configured to face the frontal cortical region of the tibia in positions spaced from the upper portion of the first contact area.

20. The surgical guide according to claim 14, wherein the front portion has an additional contact area extending, according to an arched extension and configured to act in abutment against the prosthetic dish along the peripheral edge thereof.

21. The surgical guide according to claim 14, wherein the front portion has at least a second pair of tibial positioning holes, respectively aligned along a direction parallel to a first direction of mutual alignment of the tibial positioning holes belonging to the first pair.

22. The surgical guide according to claim 14, wherein at least one of either the first or the second contact area subtends an arc greater than 90° about a longitudinal axis of the tibia along the peripheral edge of the prosthetic dish.

23. The surgical guide according to claim 14, wherein the proximal portion has an end edge projecting onto the working surface of the prosthetic dish and extending parallel to the peripheral edge of the prosthetic dish itself.

24. The surgical guide according to claim 14, wherein the second contact area extends along the peripheral edge of the prosthetic dish.

25. The surgical guide according to claim 14, wherein the front portion has two arms projecting onto the working surface of the prosthetic dish and bearing respective terminal portions configured to act against the working surface itself at the second contact area.

26. The surgical guide according to claim 24, wherein the second contact area extends along a whole extension of at least one of the said arms, continuously with the first contact area.

27. The surgical guide according to claim 14, wherein the proximal portion of the tibial component has a tibial centering housing configured to guide insertion of a bore cutter along the longitudinal axis of the tibia.

28. The surgical guide according to claim 27, wherein the tibial centering housing is directly formed in the proximal portion.

29. The surgical guide according to claim 27, wherein the tibial centering housing is formed in a tibial insert that can be removably engaged with the tibial component.

30. A surgical method of using the surgical guide of claim 14 in a total prosthetic knee revision, further comprising:
   exclusively coupling a tibial component of the surgical guide against the proximal end of the tibia, the tibia component comprising:
      a front portion having a first contact area configured to act in abutment against a front cortical region of the tibial bone part;
      a proximal portion projecting in cantilever fashion on a continuation of the front portion and having at least one second contact area configured to act in abutment against a working surface of the prosthetic dish surrounded by a peripheral edge of the prosthetic dish itself,
   wherein the front portion has at least one first pair of tibial positioning holes configured to face the front cortical region of the tibia, when the tibial component is coupled with the proximal end of the tibia,
   wherein the tibial component is configured to exclusively couple with the proximal end of a tibia bearing a prosthetic dish attached to a tibial bone part;
   inserting at least two tibial alignment pins into the tibial positioning holes of the tibial component and through the tibia's front cortical region;
   removing the tibial component from the proximal end of the tibia;
   removing a tibial prosthesis from the proximal end of the tibia;
   engaging a tibial resection block on the tibial positioning pins;
   performing a proximal resection of the tibial bone part while the tibial component is engaged on the tibial positioning pins;
   removing the tibial alignment pins; and
   positioning a revision tibial prosthesis on the proximal end of the tibia.

31. A surgical method of using the surgical guide of claim 1 in a total prosthetic knee revision, comprising:
   exclusively coupling the femoral component against the distal end of a patient's femur;
   inserting at least two alignment pins into the guide holes of the femoral component and through a front cortical region of the femur;
   removing the femoral component from the distal end of the femur;
   removing the femoral prosthesis from the distal end of the femur;
   engaging said guide holes along the alignment pins to exclusively re-couple the femoral component to the distal end of the femur;
   preparing attachment holes through the femoral bone part, using a drilling tool guided through the frontal positioning holes and the distal positioning holes of the femoral component;
   removing the femoral component from the distal end of the femur;
   engaging frontal and distal positioning pins in the frontal and distal positioning holes, respectively;
   engaging a distal cutting block on the frontal positioning pins;
   performing a distal femoral bone resection while the distal cutting block is engaged on the frontal positioning pins;
   engaging a frontal cutting block on the distal positioning pins;
   performing a frontal resection of the femoral bone part while the frontal cutting block is engaged on the distal positioning pins;
   removing the frontal and distal positioning pins;
   positioning a revision femoral prosthesis on the distal end of the femur.

\* \* \* \* \*